United States Patent
Yamada et al.

(10) Patent No.: US 9,816,961 B2
(45) Date of Patent: *Nov. 14, 2017

(54) GAS SENSOR CONTROL APPARATUS

(71) Applicant: DENSO CORPORATION, Kariya, Aichi-pref. (JP)

(72) Inventors: Yuji Yamada, Nagoya (JP); Mikiyasu Matsuoka, Obu (JP); Kenichi Ono, Kariya (JP); Takamasa Oguri, Toyoake (JP); Takao Mishima, Kariya (JP)

(73) Assignee: DENSO CORPORATION, Kariya (JP)

( * ) Notice: Subject to any disclaimer, the term of this patent is extended or adjusted under 35 U.S.C. 154(b) by 669 days.

This patent is subject to a terminal disclaimer.

(21) Appl. No.: 14/455,051

(22) Filed: Aug. 8, 2014

(65) Prior Publication Data

US 2015/0041318 A1 Feb. 12, 2015

(30) Foreign Application Priority Data

Aug. 9, 2013 (JP) .................. 2013-167125

(51) Int. Cl.
*G01N 27/409* (2006.01)
*F01N 3/10* (2006.01)
*F01N 11/00* (2006.01)

(52) U.S. Cl.
CPC ........... *G01N 27/409* (2013.01); *F01N 3/101* (2013.01); *F01N 11/007* (2013.01); *F01N 2900/1402* (2013.01); *Y02T 10/22* (2013.01)

(58) Field of Classification Search
None
See application file for complete search history.

(56) References Cited

U.S. PATENT DOCUMENTS 5,203,983 A * 4/1993 Ohyama ............ G01N 27/4065
                                                        204/424
5,810,997 A * 9/1998 Okazaki .............. G01N 27/407
                                                        204/425

(Continued)

FOREIGN PATENT DOCUMENTS

| JP | 56-59127 A | 5/1981 |
|---|---|---|
| JP | 2008-032712 A | 2/2008 |
| JP | 2013-177884 A | 9/2013 |

OTHER PUBLICATIONS

Japanese Office Action dated Jul. 14, 2015 in the corresponding JP application No. 2013-167125. (English translation attached).

(Continued)

*Primary Examiner* — Luan Van
*Assistant Examiner* — Steven E Rosenwald
(74) *Attorney, Agent, or Firm* — Posz Law Group, PLC

(57) ABSTRACT

An $O_2$ sensor has a sensor element, which includes a solid electrolyte layer and a pair of electrodes. The solid electrolyte layer is held between the electrodes. The electrodes include an atmosphere side electrode, which becomes a positive side at a time of outputting an electromotive force from the sensor element, and an exhaust side electrode, which becomes a negative side at the time of outputting the electromotive force from the sensor element. A resistor is provided in an electric path that connects between the atmosphere side electrode and a ground. When the sensor element generates the electromotive force, the resistor conducts an electric current, which is generated while using the electromotive force as an electric power source, to induce a change in an output characteristic of the $O_2$ sensor.

8 Claims, 8 Drawing Sheets

(56) References Cited

U.S. PATENT DOCUMENTS

2012/0043205 A1* 2/2012 Matsuoka ............ G01N 27/407
204/410
2013/0180853 A1* 7/2013 Mori ................... F02D 41/1455
204/406

OTHER PUBLICATIONS

U.S. Appl. No. 14/455,089, filed Aug. 8, 2014, Yamada et al.
U.S. Appl. No. 14/454,769, filed Aug. 8, 2014, Yamada et al.
U.S. Appl. No. 14/454,792, filed Aug. 8, 2014, Matsuoka et al.

* cited by examiner

GAS SENSOR CONTROL APPARATUS

CROSS REFERENCE TO RELATED APPLICATION

This application is based on and incorporates herein by reference Japanese Patent Application No. 2013-167125 filed on Aug. 9, 2013.

TECHNICAL FIELD

The present invention relates to a gas sensor control apparatus.

BACKGROUND

For instance, a gas sensor, which outputs an electromotive force, is provided at a vehicle engine (e.g., an automobile engine). In this type of gas sensor, exhaust gas, which is discharged from the engine, serves as a sensing subject of the gas sensor, and an oxygen concentration of the exhaust gas is sensed with the gas sensor. This type of gas sensor includes an electromotive force cell, which outputs an electromotive force signal that varies depending on whether the exhaust gas is rich or lean. Specifically, when an air-to-fuel ratio is rich, the electromotive force cell outputs the electromotive force signal of about 0.9 V. In contrast, when the air-to-fuel ratio is lean, the electromotive force cell outputs the electromotive force signal of about 0 V.

In this type of gas sensor, when the air-to-fuel ratio of the exhaust gas changes between rich and lean, a change in the sensor output may be disadvantageously delayed relative to an actual change in the air-to-fuel ratio. In order to improve the output characteristic of such a gas sensor, various techniques have been proposed.

For instance, JP2012-063345A (corresponding to US2012/0043205A1) discloses a gas sensor control apparatus, in which a constant current circuit is connected to at least one of a pair of sensor electrodes (i.e., two sensor electrodes). In this gas sensor control apparatus, when it is determined that a demand for changing the output characteristic of the gas sensor is present, a flow direction of the constant electric current is determined based on the demand. Then, the constant current circuit is controlled to supply the constant electric current in the determined direction. Specifically, the constant current circuit can supply the constant electric current in any one of a forward direction and a backward direction and can adjust a current value of the electric current through a pulse width modulation (PWM) control operation.

However, in the above-describe technique, the supply of the constant electric current of the constant current circuit is controlled through the PWM control operation. In order to meet, for example, a cost reduction demand, an improvement may be made to simplify the structure.

SUMMARY

The present disclosure is made in view of the above disadvantage.

According to the present disclosure, there is provided a gas sensor control apparatus for a gas sensor that outputs an electromotive force signal corresponding to an air-to-fuel ratio of an exhaust gas of an internal combustion engine and includes an electromotive force cell, which has a solid electrolyte body and a pair of electrodes. The solid electrolyte body is held between the pair of electrodes that include a reference side electrode, which becomes a positive side at a time of outputting an electromotive force from the electromotive force cell, and an exhaust side electrode, which becomes a negative side at the time of outputting the electromotive force from the electromotive force cell. The gas sensor control apparatus includes a resistor that is installed in an electric path, which is connected to the electromotive force cell. When the electromotive force cell generates the electromotive force, the resistor conducts an electric current, which is generated while using the electromotive force of the electromotive force cell as an electric power source, to induce a change in an output characteristic of the gas sensor.

BRIEF DESCRIPTION OF THE DRAWINGS

The drawings described herein are for illustration purposes only and are not intended to limit the scope of the present disclosure in any way.

DETAILED DESCRIPTION

Figure 1:
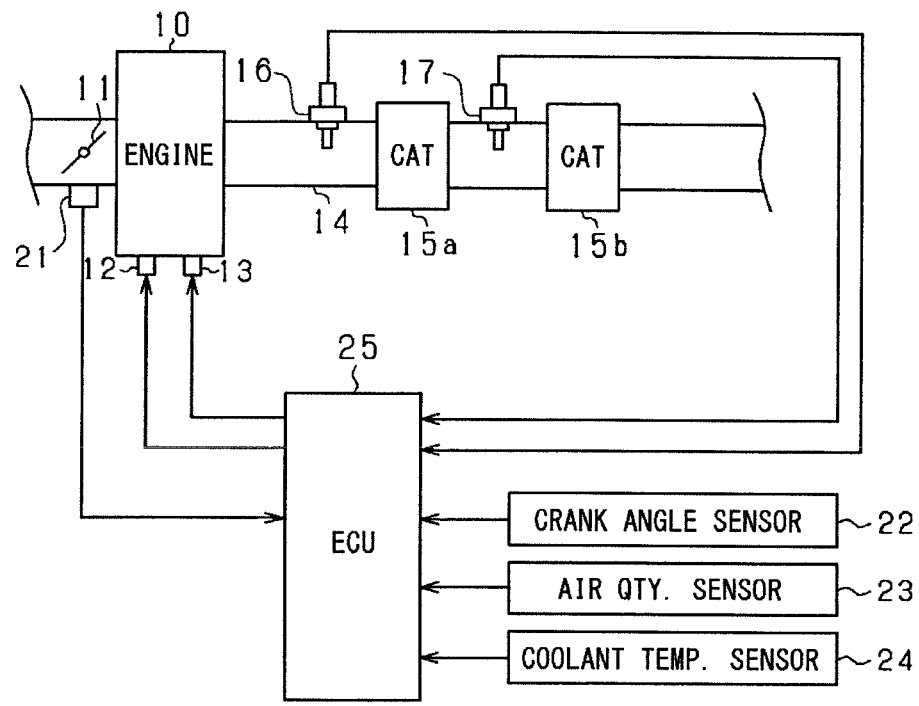
FIG. 1 is a diagram schematically showing an entire structure of an engine control system according to an embodiment of the present disclosure.

An embodiment of the present disclosure will be described with reference to the accompanying drawings. In the present embodiment, a gas sensor, which is provided in an exhaust conduit of an engine (internal combustion engine) of a vehicle (e.g., an automobile), is used, and there will be described an engine control system, which executes various control operations of the engine based on an output of the gas sensor, In the engine control system, an electronic control unit (hereinafter referred to as an ECU) is used to execute, for example, a control operation of a fuel injection quantity and a control operation of ignition timing. FIG. 1 is a diagram that schematically shows an entire structure of the engine control system.

In FIG. 1, the engine 10 is, for example, a gasoline engine and has an electronically controlled throttle valve 11, fuel injection valves 12, and ignition devices 13. Catalysts (also referred to as catalytic converters) 15a, 15b, which serve as an exhaust gas purifying device, are installed in an exhaust conduit 14 (serving as an exhaust device) of the engine 10. Each of the catalysts 15a, 15b is formed as, for example, a three-way catalyst. The catalyst 153 is a first catalyst, which serves as an upstream side catalyst, and the catalyst 15b is a second catalyst, which serves as a downstream side catalyst. As is well known in the art, the three-way catalyst purifies three noxious components of the exhaust gas, i.e., CO (carbon monoxide), HC (hydrocarbon) and NOx (nitrogen oxide, such as NO) and is formed by applying metal, such as platinum, palladium, rhodium, to a ceramic substrate that is configured into, for example, a honeycomb form or a lattice form. In this instance, at the three-way catalyst, CO and HC, which are the rich components, are purified through an oxidation reaction, and NOx, which is the lean component, is purified through a reduction reaction.

An air-to-fuel ratio (A/F) sensor 16 is placed on an upstream side of the first catalyst 15a in a flow direction of the exhaust gas, and an oxygen ($O_2$) sensor 17 is placed between the first catalyst 15a and the second catalyst 15b, i.e., is placed on the downstream side of the first catalyst 15a and on the upstream side of the second catalyst 15b in the flow direction of the exhaust gas. The A/F sensor 16 outputs an NF signal, which is generally proportional to the air-to-fuel ratio of the exhaust gas. Furthermore, the $O_2$ sensor 17 outputs an electromotive force (EMF) signal, which varies depending on whether the air-to-fuel ratio of the exhaust gas is rich or lean.

Furthermore, various sensors, such as a throttle opening degree sensor 21, a crank angle sensor 22, an air quantity sensor 23 and a coolant temperature sensor 24, are installed in the engine control system. The throttle opening degree sensor 21 senses the opening degree of the throttle valve 11. The crank angle sensor 22 outputs a crank angle signal of a rectangular waveform at every predetermined crank angle (e.g., a period of 30 degree crank angle) of the engine 10. The air quantity sensor 23 senses the quantity of the intake air drawn into the engine 10. The coolant temperature sensor 24 senses the temperature of the engine coolant. Although not depicted in the drawings, besides the above sensors, there are also provided, for example, a combustion pressure sensor, which senses a combustion pressure in a cylinder of the engine, an accelerator opening degree sensor, which senses an opening degree of an accelerator (an accelerator manipulation amount or an amount of depression of an accelerator pedal), and an oil temperature sensor, which senses a temperature of an engine lubricating oil. These sensors respectively serve as an operational state sensing means.

The ECU 25 includes a microcomputer of a known type, which has a CPU, a ROM, and a RAM (memories). The ECU 25 executes various control programs, which are stored in the ROM, to perform various control operations of the engine 10 according to the engine operational state. Specifically, the ECU 25 receives signals from the above-described sensors, and the ECU 25 computes each corresponding fuel injection quantity and each corresponding ignition timing to execute, for example, the control operation for driving the fuel injection valves 12 and the control operation for driving the ignition devices 13 based on the signals.

Particularly, with respect to the fuel injection quantity control operation, the ECU 25 performs an air-to-fuel ratio feedback control operation based on a measurement signal of the A/F sensor 16, which is placed on the upstream side of the first catalyst 15a, and a measurement signal of the $O_2$ sensor 17, which is placed on the downstream side of the first catalyst 15a. Specifically, the ECU 25 executes a main feedback control operation in such a manner that an actual air-to-fuel ratio (an actual air-to-fuel ratio at the location on the upstream side of the first catalyst 15a), which is sensed with the A/F sensor 16, coincides with a target air-to-fuel ratio, which is set based on the engine operational state. Also, the ECU 25 executes a sub-feedback control operation in such a manner that an actual air-to-fuel ratio (an actual air-to-fuel ratio at the location on the downstream side of the first catalyst 15a), which is sensed with the $O_2$ sensor 17, coincides with the target air-to-fuel ratio. In the sub-feedback control operation, in view of, for example, a difference between the actual air-to-fuel ratio on the downstream side of the first catalyst 15a and the target air-to-fuel ratio, the target air-to-fuel ratio used in the main feedback control operation is corrected, or a feedback correction amount used in the main feedback control operation is corrected. The ECU 25 executes a stoichiometric feedback control operation, which sets the target air-to-fuel ratio to a stoichiometric air-to-fuel ratio, as the air-to-fuel ratio control operation.

Figure 2:
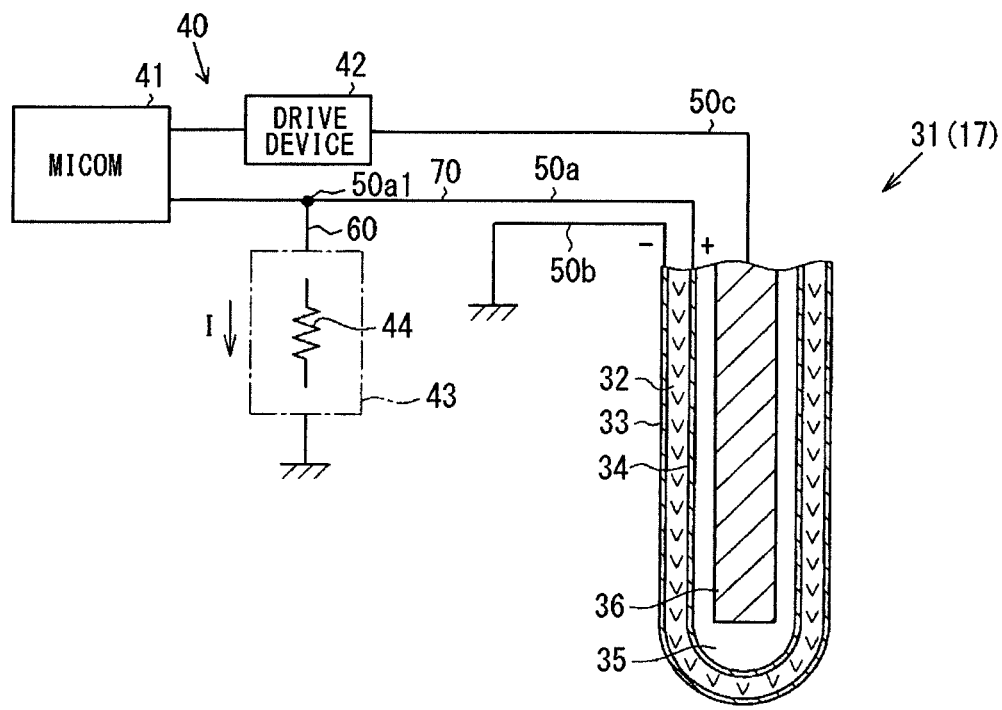
FIG. 2 is a diagram schematically showing a cross section of a sensor element and a sensor control arrangement of the embodiment.

Next, the structure of the $O_2$ sensor 17, which is placed on the downstream side of the first catalyst 15a, will be described. The $O_2$ sensor 17 has a sensor element (also referred to as a sensing device) 31, which is configured into a cup shape. FIG. 2 shows a cross section of the sensor element 31. In reality, the sensor element 31 is configured such that the entire sensor element 31 is received in a housing or an element cover, and the sensor element 31 is placed in the engine exhaust conduit 14. The sensor element 31 serves as an electromotive force cell, In the sensor element 31, a solid electrolyte layer (serving as a solid electrolyte body) 32 has a cup shaped cross section. An exhaust side electrode 33 is formed in an outer surface of the solid electrolyte layer 32, and an atmosphere side electrode 34 is formed in an inner surface of the solid electrolyte layer 32. Each of the electrodes 33, 34 is formed as a layer on the corresponding one of the outer surface and the inner surface of the solid electrolyte layer 32. The solid electrolyte layer 32 is an oxide sintered body, which conducts oxygen ions therethrough and is formed by completely dissolving CaO, MgO, $Y_2O_3$, and/or $Yb_2O_3$ as stabilizer into $ZrO_2$, $HfO_2$, $ThO_2$, and/or $Bi_2O_3$. Furthermore, each electrode 33, 34 is made of a noble metal, such as platinum, which has the high catalytic activity, and a surface of the electrode 33, 34 is covered with a porous coating that is chemically plated. The above-described two electrodes 33, 34 serve as a pair of electrodes (sensor electrodes). An inside space, which is surrounded by the solid electrolyte layer 32, is an atmosphere chamber (a reference gas chamber or simply referred to as a reference chamber) 35. A heater 36 is received in the atmosphere chamber 35. The heater 36 has a sufficient heat capacity to activate the sensor element 31, and the sensor element 31 is entirely heated by a heat energy, which is generated from the heater 36. An activation temperature of the $O_2$ sensor 17 is, for example, 500 to 650 degrees Celsius. The atmosphere gas (atmosphere air) is introduced into the atmosphere chamber 35, so that the inside of the atmosphere chamber 35 is maintained at a predetermined oxygen concentration.

In the sensor element 31, the exhaust gas is present at the outside (the electrode 33 side) of the solid electrolyte layer 32, and the atmosphere gas (atmosphere air) is present at the inside (the electrode 34 side) of the solid electrolyte layer 32. An electromotive force is generated between the electrode 33 and the electrode 34 in response to a difference in an oxygen concentration (a difference in an oxygen partial pressure) between the outside (the electrode 33 side) of the solid electrolyte layer 32 and the inside (the electrode 34 side) of the solid electrolyte layer 32. Specifically, the generated electromotive force varies depending on whether the air-to-fuel ratio is rich or lean. In such a case, the oxygen concentration at the exhaust side electrode 33 is lower than the oxygen concentration at the atmosphere side electrode 34, which serves as a reference side electrode, and the electromotive force is generated at the sensor element 31 while the atmosphere side electrode 34 and the exhaust side electrode 33 serve as a positive side and a negative side, respectively. In this instance, the exhaust side electrode 33 is grounded through an electric path 50b, as shown in FIG. 2. Thus, the 02 sensor 17 outputs the electromotive force signal, which corresponds to the oxygen concentration (the air-to-fuel ratio) of the exhaust gas.

Figure 3:
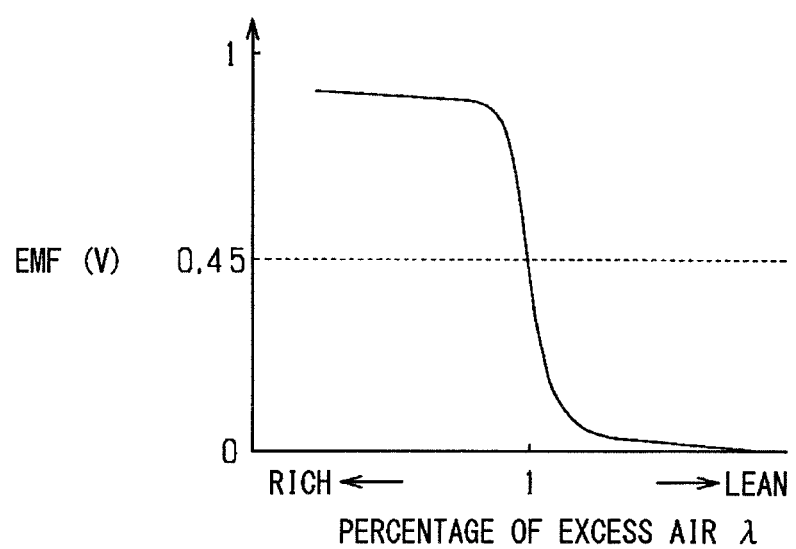
FIG. 3 is an electromotive force characteristic diagram indicating a relationship between an air-to-fuel ratio and an electromotive force of the sensor element.

FIG. 3 is an electromotive force characteristic diagram showing a relationship between the air-to-fuel ratio of the exhaust gas and the electromotive force of the sensor element 31. In FIG. 3, the axis of abscissas indicates a percentage of excess air λ. When the percentage of excess air λ is 1 (i.e., λ=1), the air-to-fuel ratio is the stoichiometric air-to-fuel ratio (stoichiometric mixture), which is also referred to as a theoretical air-to-fuel ratio. The sensor element 31 has the characteristics of that the electromotive force generated from the sensor element 31 varies depending on whether the air-to-fuel ratio is rich or lean, and the electromotive force generated from the sensor element 31 rapidly changes around the stoichiometric air-to-fuel ratio. Specifically, the electromotive force (also referred to as a sensor electromotive force) of the sensor element 31 at the rich time is about 0.9 V, and the electromotive force of the sensor element 31 at the lean time is about 0 V.

In FIG. 2, a sensor control arrangement (also referred to as a sensor control apparatus) 40 is connected to the sensor element 31. When the electromotive force is generated at the sensor element 31 in response to the air-to-fuel ratio (the oxygen concentration) of the exhaust gas, the sensor measurement signal (the electromotive force signal), which corresponds to the electromotive force generated at the sensor element 31 is outputted from the sensor element 31 to a microcomputer 41 of the sensor control arrangement 40 through the electric path 50a. The microcomputer 41 has a CPU, a ROM, and a RAM (memories) and executes various operations upon execution of each corresponding program stored in one or more of the memories. The microcomputer 41 computes the air-to-fuel ratio based on the electromotive force signal of the sensor element 31. The sensor control arrangement 40 is formed in the ECU 25 of FIG. 1. At the ECU 25, the microcomputer 41 is formed as a computing device (computing means) that has an engine control function and a sensor control function. In this case, the microcomputer 41 computes the engine rotational speed and the intake air quantity based on the measurement results of the various sensors. However, instead of having the single microcomputer, the ECU 25 may be constructed to have an engine control microcomputer, which executes the engine control function, and a sensor control microcomputer, which executes the sensor control function, if desired.

Furthermore, the microcomputer 41 determines an activated state of the sensor element 31 and controls the driving operation of the heater 36 through a drive device 42, which is connected to the heater 36 through an electric path 50c, based on a result of determination of the activated state of the sensor element 31. The technique of the activation determination of the sensor element 31 and the technique of the heater control are already known. Therefore, the activation determination of the sensor element 31 and the heater control will be briefly described. The microcomputer 41 periodically changes the voltage or the electric current applied to the sensor element 31 in a manner that is similar to an alternating current and senses a thus generated change in the electric current or a thus generated change in the electric voltage. A resistance of the sensor element 31 (an impedance of the sensor element 31) is computed based on the change in the electric current or the change in the voltage, and the energization control operation of the heater 36 is executed based on the resistance of the sensor element 31. At that time, there is a correlation between the activated state of the sensor element 31 (the temperature of the sensor element 31) and the resistance of the sensor element 31. When the resistance of the sensor element 31 is controlled to a predetermined target value, the sensor element 31 is held in the desired activated state (the state, under which the activation temperature of the sensor element 31 is held in a range of 500 to 650 degrees Celsius). For example, a sensor element temperature feedback control operation may be executed as the heater control operation.

When the engine 10 is operated, the actual air-to-fuel ratio of the exhaust gas is changed. For example, the air-to-fuel ratio may be repeatedly changed between rich and lean. At the time of changing the actual air-to-fuel ratio between rich and lean, when a deviation exists between the output of the $O_2$ sensor 17 and the presence of NOx, which is the lean component, the emission performance may possibly be influenced. For example, the amount of NOx in the exhaust gas may possibly be increased beyond the intended amount at the time of operating the engine 10 under the high load (the time of accelerating the vehicle).

Figure 4:
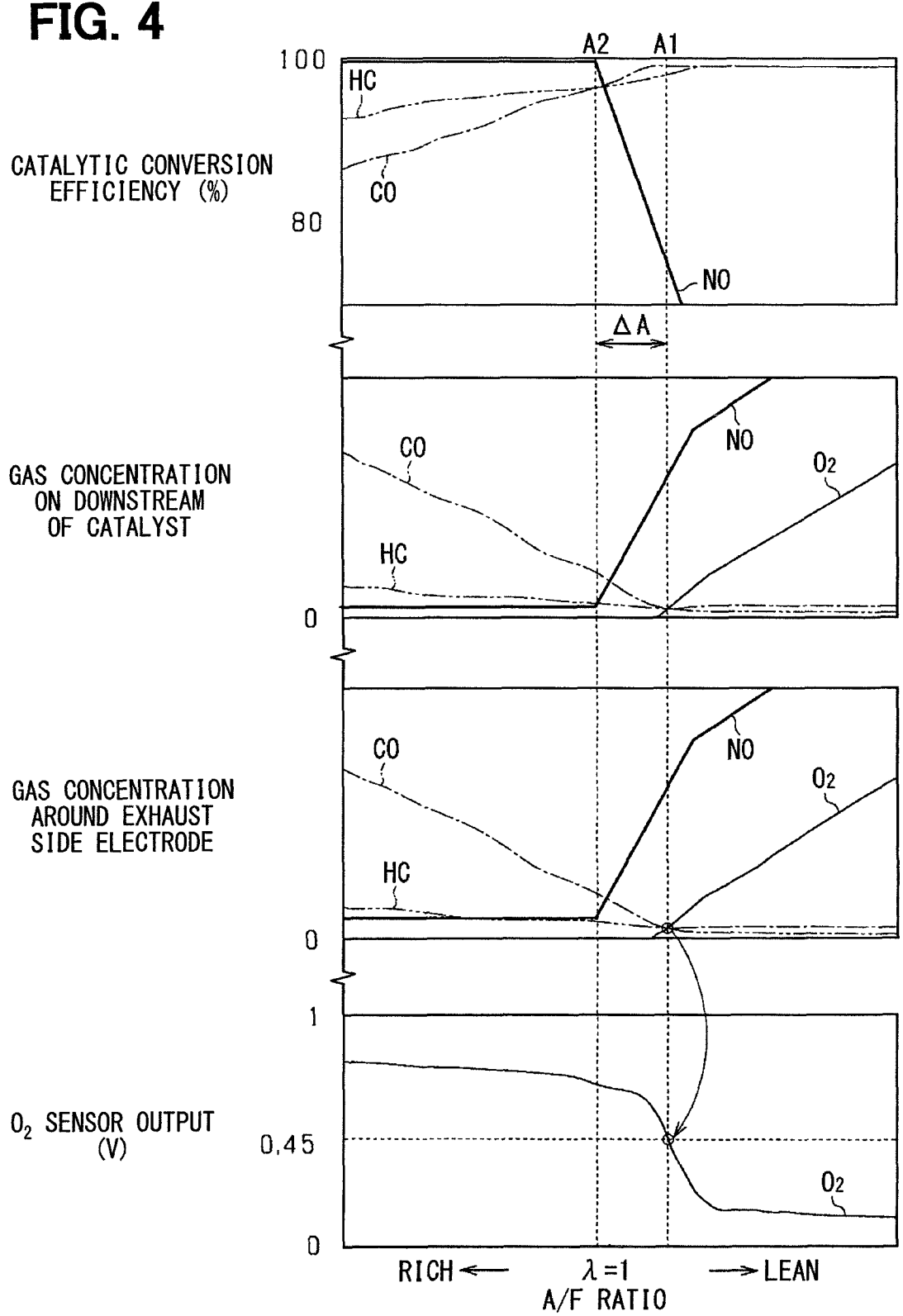
FIG. 4 is a diagram showing a catalytic conversion efficiency of a first catalyst and output characteristics of an $O_2$ sensor.

In the present embodiment, a sensing mode of the $O_2$ sensor 17 is changed based on the relationship between the output characteristic of the $O_2$ sensor 17, which outputs the electromotive force, and the exhaust gas purifying characteristic of the first catalyst 15a, which is placed on the upstream side of the $O_2$ sensor 17. Details of the change of the sensing mode of the $O_2$ sensor 17 will be described later. FIG. 4 is a diagram that shows the catalytic conversion characteristics of the first catalyst 15a, which is the three-way catalyst, and the output characteristics of the $O_2$ sensor 17. Specifically, FIG. 4 shows: (I) a relationship between a catalytic conversion efficiency of each of the three noxious components (i.e., CO, HC, NOx) of the exhaust gas at the first catalyst 15a and the air-to-fuel ratio; (II) a relationship between the gas concentration of each of the three noxious components and the oxygen on the downstream side of the first catalyst 15a and the air-to-fuel ratio; (III) a relationship between the gas concentration of each of the three noxious components and the oxygen around the surface of the exhaust side electrode 33 of the $O_2$ sensor 17 and the air-to-fuel ratio; and (IV) a relationship between the electromotive force output of the $O_2$ sensor 17 and the air-to-fuel ratio.

The first catalyst (the three-way catalyst) 15a has a catalytic conversion window, in which the catalytic conversion efficiency of each of the three noxious components becomes high around the point of the stoichiometric air-to-fuel ratio (percentage of excess air λ=1), as is known in the art. Furthermore, with respect to the concentrations of the three noxious components and the concentration of the oxygen on the downstream side of the first catalyst 15a, it is understood that a reaction equilibrium point A1, at which the concentrations of the rich components (CO, HC) and the concentration of the oxygen become generally equal to one another, is present around the point of the stoichiometric air-to-fuel ratio, and an NOx outflow point A2, at which NOx (NO) begins to outflow from the first catalyst 15a on the downstream side of the first catalyst 15a, is also present. In this case, the NOx outflow point A2 (the point of starting the outflow of NOx from the catalyst 15a) is located on the rich side of the reaction equilibrium point A1, and the NOx outflow point A2 and the reaction equilibrium point A1 are spaced from each other by a difference ΔA. That is, the first catalyst 15a has the catalytic conversion characteristic of that the NOx outflow point (serving as a second air-to-fuel ratio point) A2, at which NOx begins to outflow from the first catalyst 15a, is located on the rich side of the reaction equilibrium point (serving as a first air-to-fuel ratio point) A1, which forms the equilibrium point for the rich components and the oxygen. The reaction equilibrium point A1 is an inflection point of the equilibrium characteristic of the rich components and the oxygen, and the NOx outflow point A2 is an inflection point of the outflow concentration characteristic of NOx.

The reason for the generation of the deviation (difference) between the point A1 and the point A2 may be as follows. In the case where the exhaust gas, which contains CO, HC, NOx, and $O_2$, is guided to the first catalyst 15a during the operation of the engine 10, NOx may possibly outflow from the first catalyst 15a in addition to CO and HC. For example, even in the range of the catalytic conversion window of the three-way catalyst, it will be noted that some amount of CO, HC, and NOx outflows from the first catalyst 15a when the amount of CO, HC, and NOx is precisely measured. In such a case, although $O_2$ outflows from the first catalyst 15a in equilibrium with CO and HC (starting of the outflow of $O_2$ at the concentration of CO and HC≈0), NOx outflows from the first catalyst 15a on the downstream side thereof regardless of the reaction of CO and HC. Therefore, the difference exists between the point A1 and the point A2.

Furthermore, the concentrations of the above three components and the oxygen around the exhaust side electrode 33 of the $O_2$ sensor 17 are the same as the concentrations of the above three components and the oxygen on the downstream side of the first catalyst 15a. In this case, the amount of the rich components (CO, HC) is larger than the amount of oxygen on the rich side of the point A1, and the amount of oxygen is larger than the amount of the rich components on the lean side of the point A1. Therefore, in terms of the electromotive force of the $O_2$ sensor 17, one of a rich signal (0.9V) and a lean signal (0V) is outputted on one side or the other side of the reaction equilibrium point A1 of the first catalyst 15a. In this case, it can be said that the reaction equilibrium point for the rich components and the oxygen at the $O_2$ sensor 17 coincides with the reaction equilibrium point A1 at the first catalyst 15a. Furthermore, NOx is present on the rich side of the point A1.

At the exhaust side electrode 33 of the $O_2$ sensor 17, the oxidation reaction and the reduction reaction of CO, HC and NOx of the exhaust gas take place according to the following chemical reaction formulae (1) to (3).

$$CO + 0.5O_2 \rightarrow CO_2 \quad (1)$$

$$CH_4 + 2O_2 \rightarrow CO_2 + 2H_2O \quad (2)$$

$$CO + NO \rightarrow CO_2 + 0.5N_2 \quad (3)$$

Furthermore, there is established a relationship of k1, k2>>K3 where k1, k2 and k3 denote an equilibrium constant of the chemical reaction formula (1), an equilibrium constant of the chemical reaction formula (2), and an equilibrium constant of the chemical reaction formula (3), respectively.

In this case, at the $O_2$ sensor 17, the equilibrium point (the point at which the electromotive force output=0.45 V) is determined through the gas reactions of, for example, CO, HC NOx, and $O_2$. However, due to the differences in the equilibrium constant, the reactions of CO and HC with $O_2$ become main reactions at the exhaust side electrode 33.

Furthermore, the above difference ΔA is present in the catalytic conversion characteristic of the first catalyst 15a, and the above difference ΔA has the influence on the output characteristic of the $O_2$ sensor 17. Therefore, even when NOx outflows from the first catalyst 15a, the output of the $O_2$ sensor 17 does not correspond to the outflow of NOx from the first catalyst 15a. Thus, the outflow of NOx from the first catalyst 15a cannot be correctly monitored, and thereby the amount of NOx emissions may possibly be increased.

Figure 5:
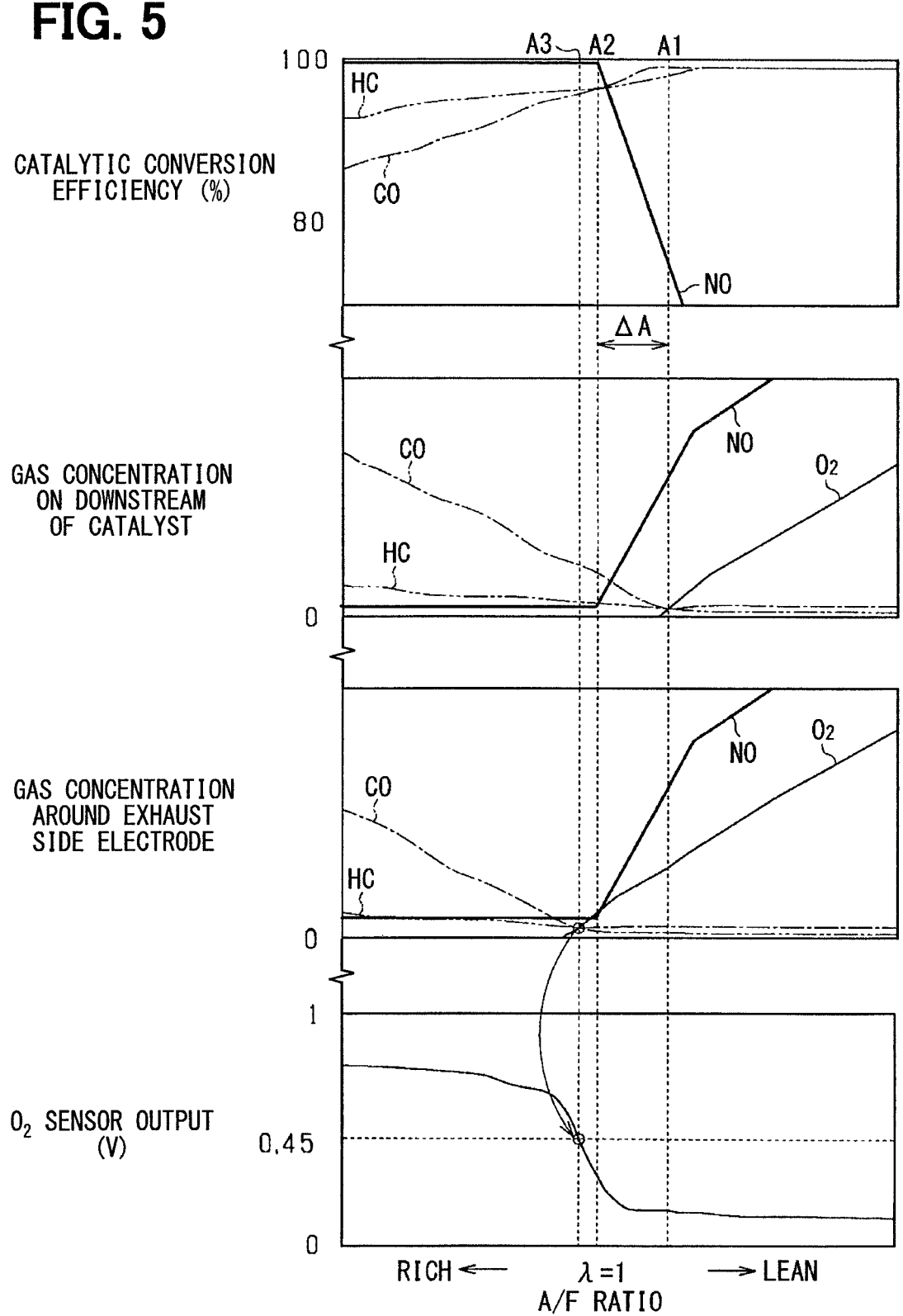
FIG. 5 is a diagram showing a catalytic conversion efficiency of a first catalyst and output characteristics of an $O_2$ sensor.

In view of the above disadvantage, according to the present embodiment, the electric current, which has a predetermined current value, is conducted between the electrodes 33, 34 of the sensor element 31 of the $O_2$ sensor 17, so that at the location around the exhaust side electrode 33 of the $O_2$ sensor 17, the concentrations of the rich components are reduced, and the concentration of the oxygen is increased. Specifically, as shown in FIG. 5, the equilibrium point of the gas reaction around the exhaust side electrode 33 of the $O_2$ sensor 17 is changed from the point A1 to a point A3. In FIG. 5, in comparison to FIG. 4, all of the concentration characteristics of CO, HC and $O_2$ around the exhaust side electrode 33 of the $O_2$ sensor 17 are shifted to the rich side. In this way, in the case where the output characteristic of the $O_2$ sensor 17 is changed, and NOx outflows from the first catalyst 15a, the output of the $O_2$ sensor 17 can correspond to the outflow of NOx.

Figure 6:
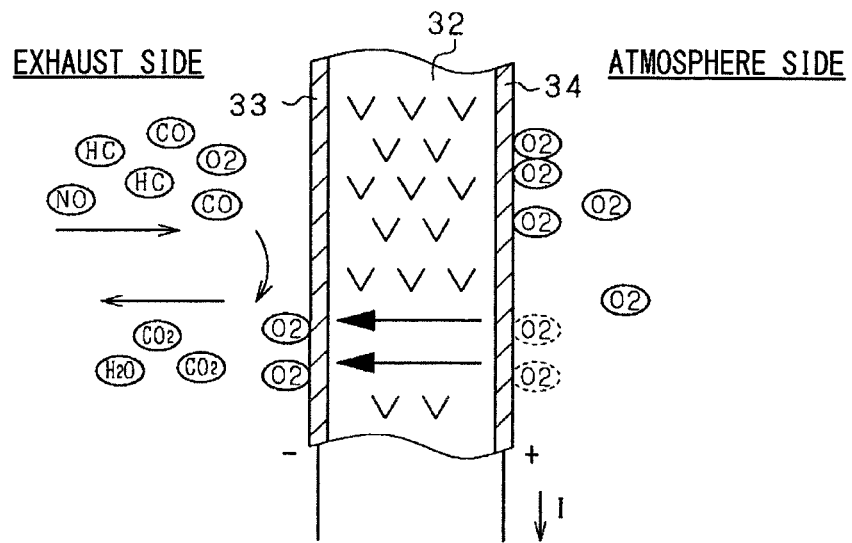
FIG. 6 is a schematic diagram for describing reactions of gas components at the sensor element.

The principle of inducing the change in the sensor output characteristic through conduction of the electric current between the electrodes 33, 34 is as follows. As shown in FIG. 6, CO, HC, NOx and $O_2$ are present around the exhaust side electrode 33 of the $O_2$ sensor 17. Under such a circumstance, the electric current is conducted through the sensor element 31 such that the oxygen ions are moved from the atmosphere side electrode 34 to the exhaust side electrode 33 through the solid electrolyte layer 32. Specifically, the oxygen pumping is executed at the sensor element 31. In this case, at the exhaust side electrode 33, the oxygen, which is moved to the exhaust side electrode 33 side through the solid electrolyte layer 32, reacts with CO and HC to form $CO_2$ and $H_2O$, respectively. In this way, CO and HC are removed around the exhaust side electrode 33, and the equilibrium point of the gas reaction around the exhaust side electrode 33 of the $O_2$ sensor 17 is shifted to the rich side.

Next, the structure of the sensor control arrangement 40, which executes the control operation with respect to the $O_2$ sensor 17, will be described. The structure of the sensor control arrangement 40 is one shown in FIG. 2. That is, the sensor control arrangement 40 includes the microcomputer 41, which serves as a control device (or control means). The microcomputer 41 obtains the electromotive force signal, which is outputted from the sensor element 31, through, for example, an analog-to-digital (A/D) converter and computes the air-to-fuel ratio (particularly, the air-to-fuel ratio on the downstream side of the first catalyst 15a) of the exhaust gas based on the obtained electromotive force signal. Furthermore, a resistor circuit (serving as a current conduction regulating device or current conduction regulating means) 43 is connected to a portion 50a1 of an electric path 50a that electrically connects between the atmosphere side electrode 34 of the sensor element 31 and the microcomputer 41. The portion 50a1 of the electric path 50a is placed in an intermediate location between the atmosphere side electrode 34 of the sensor element 31 and the microcomputer 41 in the electric path 50a. The resistor circuit 43 is configured to induce a flow of an electric current through the sensor element 31 when the sensor element 31 generates the electromotive force.

The resistor circuit 43 is a current conducting circuit that conducts the electric current, which corresponds to the electromotive force of the sensor element 31, when the electromotive force of the sensor element 31 is applied to the resistor circuit 43. The resistor circuit 43 includes a resistor 44, which is installed in an electric path 60 that connects between the atmosphere side electrode 34 of the $O_2$ sensor 17 and a ground (earth), more specifically, between the portion 50a1 of the electric path 50a and the ground, as shown in FIG. 2. The electric path 50a and the electric path 60 cooperate together to form an electric path 70 that connects between the atmosphere side electrode 34 of the $O_2$ sensor 17 and the ground (earth). The resistor 44 serves as a current conducting resistor. In this case, when the electric current I flows through the resistor 44 in the electric path 60 to the ground, the corresponding electric current flows from the exhaust side electrode 33 to the atmosphere side electrode 34 through the solid electrolyte layer 32 in the sensor element 31, and thereby the oxygen ions move from the atmosphere side electrode 34 to the exhaust side electrode 33 through the solid electrolyte layer 32 in the sensor element 31. Here, the electromotive force of the sensor element 31 is used as an electric power source of the electric current I conducted through the resistor 44 in the electric path 60.

In the present embodiment, the electric current (more specifically a current value of the electric current), which is supplied to the sensor element 31, is determined in view of the deviation, i.e., difference between the reaction equilibrium point A1 of the oxygen outflow at the first catalyst 15a and the NOx outflow point A2 of the NOx outflow at the first catalyst 15a. Then, this determined electric current is supplied to the sensor element 31, so that a change in the output characteristic, which corresponds to the difference between the reaction equilibrium point A1 and the NOx outflow point A2, is made at an intermediate point (0.45 V in the present embodiment) of the output characteristic of the $O_2$ sensor 17. That is, the electric current is supplied to the sensor element 31 such that the equilibrium point of the gas reaction around the exhaust side electrode 33 of the $O_2$ sensor 17 is placed at the NOx outflow point A2 or a point adjacent to the NOx outflow point A2. In this way, the output characteristic of the $O_2$ sensor 17 is changed based on the catalytic conversion efficiency of the first catalyst 16a. Thereby, when NOx outflows from the first catalyst 15a, the lean signal is outputted at the $O_2$ sensor 17 from the beginning of the outflow of NOx from the first catalyst 15a.

Here, in view of ensuring the robustness of the $O_2$ sensor 17 for the purpose of limiting the NOx emissions, it is desirable that the equilibrium point of the gas reaction around the exhaust side electrode 33 of the $O_2$ sensor 17 is placed on the rich side of the NOx outflow point A2 (see FIG. 5). Specifically, the equilibrium point of the gas reaction around the exhaust side electrode of the $O_2$ sensor 17 may be shifted from the NOx outflow point A2 on the rich side of the NOx outflow point A2 by the amount of, for example, about 0.1 to 0.5% (more desirably 0.1 to 0.3%) in terms of the percentage of excess air λ to have a slightly rich state.

Figure 7:
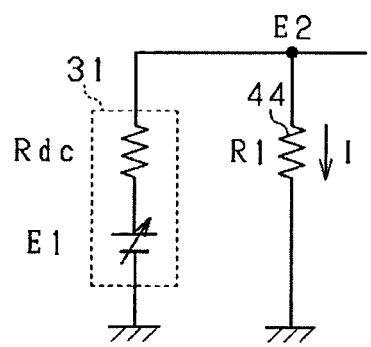
FIG. 7 is a diagram showing an equivalent circuit of the sensor element and a resistor.

In the present embodiment, a range of the electric current (more specifically a range of the current value of the electric current) is set to be 0.1 mA to 1.0 mA, and the electric current in the range of 0.1 mA to 1.0 mA is supplied to the sensor element 31. Hereinafter, a practically desirable range of a resistance value of the resistor 44 will be verified in the case where the range of the electric current (the range of the current value of the electric current) is 0.1 mA to 1.0 mA. FIG. 7 is an equivalent circuit of the sensor element 31 and the resistor 44. In FIG. 7, E1 is an electromotive force of the sensor element 31, and Rdc is a resistance value of the sensor element 31. Furthermore, E2 is a voltage of an intermediate point between the sensor element 31 and the resistor 44 in the electric path 70, and R1 is a resistance value of the resistor 44. In this instance, the resistance value Rdc is supposed to be in a range of 50Ω to 200Ω, which is the resistance value of the sensor element 31 that is in the activated state. In the equivalent circuit of FIG. 7, the following relationships are satisfied.

$$E2 = E1 \times (R1/(Rdc+R1))$$

$$I = E2/R1$$

First of all, there will be described an exemplary case where the output characteristic of the $O_2$ sensor 17 at the stoichiometric point is changed in the corresponding range of electric current=0.1 mA to 1.0 mA. In this case, Rdc=50Ω to 200Ω. E1=0.45 V, and I=0.1 mA to 1.0 mA are set, and a minimum possible value of the resistance value R1 is R1=250Ω (in the case where Rdc=200Ω, E1=0.45 V, and I=1.0 mA are set). Furthermore, a maximum possible value of the resistance value R1 is R1=4450Ω (in the case where Rdc=50Ω, E1=0.45 V, and I=0.1 mA are set). Thus, it is desirable to set the resistance value R1 of the resistor 44 in the range of about 250Ω to 4.5 kΩ.

Furthermore, there will be described an exemplary case where the output characteristic of the $O_2$ sensor 17 in the rich side is changed in the range of electric current=0.1 mA to 1.0 mA. In this case. Rdc=50Ω to 200Ω, E1=1.0 V, and I=0.1 mA to 1.0 mA are set, and a minimum possible value of the resistance value R1 is R1=800Ω (in the case where Rdc=200Ω, E1=1.0 V, and I=1.0 mA are set). Furthermore, a maximum possible value of the resistance value R1 is R1=9950Ω (in the case where Rdc=50Ω, E1=1.0 V, and I=0.1 mA are set). Thus, it is desirable to set the resistance value R1 of the resistor 44 in the range of about 800Ω to 10Ω. In a case where the electromotive force E1 at the rich time is assumed to be E1=0.9 V, the range of the resistance value R1 of the resistor 44 is about 700Ω to 9 kΩ.

In view of implementing the appropriate change in the output characteristic at the $O_2$ sensor 17 in the range of the stoichiometric point to the rich side, an appropriate range of the resistance value R1 of the resistor 44 is supposed to be about 800Ω to 4.5 kΩ. However, in a case where the appropriate range of the resistance value R1 of the resistor 44 is estimated within a possible wider range, the appropriate range of the resistance value R1 of the resistor 44 may be about 200Ω to 10 kΩ.

Figure 8:
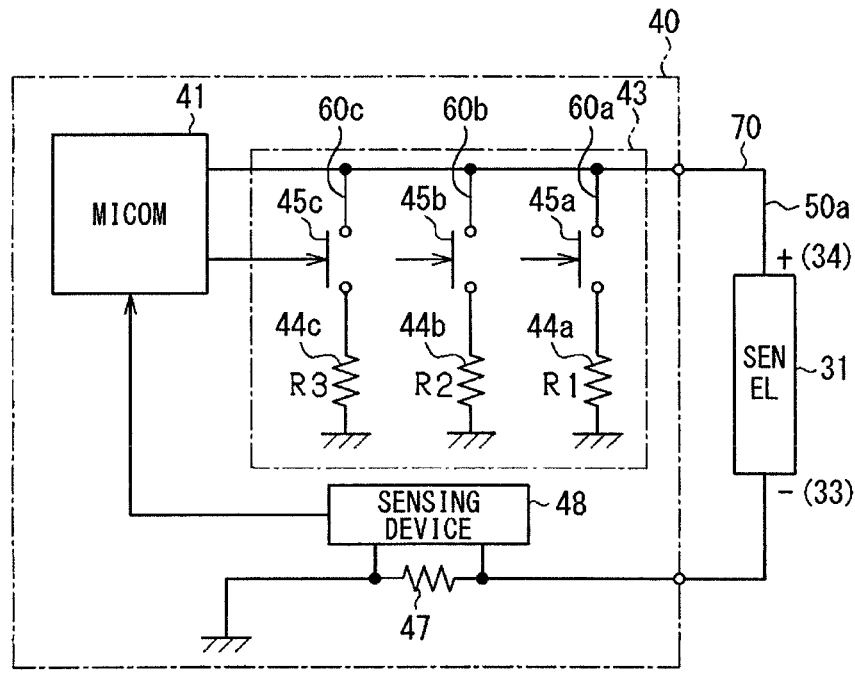
FIG. 8 is a diagram showing a structure of the sensor control arrangement.

Next, the resistor circuit 43 of the sensor control arrangement 40 and its peripheral circuit will be described in detail with reference to FIG. 8. In the structure of FIG. 8, the resistance value of the resistor circuit 43 is variably controllable, and the resistance value of the resistor circuit 43 is varied, i.e., changed according to a demand for changing the resistance value.

In the sensor control arrangement 40, the resistor circuit 43 includes a plurality of electric paths 60a-60c, each of which is provided as the electric path 60 of FIG. 2 and connects between the atmosphere side electrode 34 of the O₂ sensor 17 and the ground (earth), more specifically, between the electric path 50a (more specifically the portion 50a1 of the electric path 50a shown in FIG. 2) and the ground. A series circuit of the switch 45 and the resistor 44 is formed in each of these electric paths 60a-60c in the resistor circuit 43. In FIG. 8, these series circuits include three series circuits. In each of these three series circuits, each of three switches 45a, 45b, 45c is provided as the switch 45, and each of three resistors 44a, 44b, 44c is provided as the resistor 44. Each of the switches 45a-45c is placed between the atmosphere side electrode 34 of the sensor element 31 and the corresponding one of the resistors 44a-44c. Each of the switches 45a-45c is a switching device (switching means) that is formed by a semiconductor switching element, such as a metal oxide semiconductor field effect transistor (MOSFET). Each of the switches 45a-45c is turned on or off in response to a command outputted from the microcomputer 41. The resistance values R1, R2, R3 of the resistors 44a-44c are different from each other. In other words, each of the resistors 44a-44c has the resistance value that is different from the resistance value of each of the rest of the resistors 44a-44c. For instance, the resistance values R1, R2, R3 may be set to satisfy a relationship of, for example, R1>E2>R3.

In such a case, the switches 45a-45c are individually on/off controlled. Depending on which one of the switches 45a-45c is turned on, the resistor to be connected to the sensor element 31 is changed among the resistors 44a-44c to change the resistance value in the resistor circuit 43. The microcomputer 41 controls the turning on/off of each switch 45a-45c based on the operational state of the engine 10.

That is, when the operational state of the engine 10 is changed, the amount of the rich components in the exhaust gas changes. Specifically, when the rotational speed of the engine is increased, or when the load of the engine is increased, the amount of the rich components in the exhaust gas is increased. In other words, when the rotational speed or the load of the engine is increased, the flow rate of the rich gas is increased, and the gas concentration of the rich gas is increased. In such a case, when the current value of the electric current to be supplied to the sensor element 31 is kept constant regardless of the engine operational state, the equilibrium point of the gas reaction around the exhaust side electrode 33 of the O₂ sensor 17 may possibly be unintentionally deviated from a desired point, which is set with reference to the NOx outflow point A2, That is, the amount of supplied oxygen, which is supplied to the location around the exhaust side electrode 33 of the sensor element 31 through the conduction of the electric current in the sensor element 31, may possibly fall short relative to the amount of the rich components, which are present around the exhaust side electrode 33 of the sensor element 31. When this shortage of the supplied oxygen occurs, the rich components remain around the exhaust side electrode 33. Thereby, the output characteristic of the O₂ sensor 17 cannot be changed in a desirable manner.

Therefore, in the present embodiment, the current value of the electric current (the resistance value of the resistor circuit 43) conducted through the sensor element 31 is variably controlled based on the operational state of the engine 10. In this case, even when the amount of required oxygen, which is required to have the equilibrium reaction of the rich gas on the surface of the exhaust side electrode 33 at the O₂ sensor 17, is changed in response to the engine operational state, the output characteristic of the O₂ sensor 17 can be changed in a desirable manner in response to the change in the required oxygen. An engine rotational speed, an engine load and/or a load rate of the engine 10 may be used as a parameter(s) of the engine operational state.

Here, it should be noted that the resistance values of the resistors 44a-44c in the resistor circuit 43 may be set to be equal to each other (i.e., R1=R2=R3), if desired. In such a case, the resistance value of the resistor circuit 43, which is connected to the sensor element 31, may be changed depending how many of the switches 45a-45c is turned on (i.e., the number of the on-state switch(es) among the switches 45a-45c), Furthermore, in the case where the output characteristic of the O₂ sensor 17 is changed by controlling the electric current (more specifically the current value of the electric current) conducted through the sensor element 31, when an abnormality occurs in, for instance, the resistor circuit 43, the exhaust emission performance is influenced. Therefore, in the present embodiment, an abnormality determining function (abnormality determining arrangement), which executes abnormality determination of the determination subject (i.e., the resistor circuit 43 in the present embodiment) is added to the microcomputer 41.

As shown in FIG. 8, a shunt resistor 47 for sensing the electric current is installed in the electric path 50b, which connects between the exhaust side electrode 33 and the ground, as a structure that is used to sense the abnormality. The electric current, which flows through the shunt resistor 47, is sensed with a current sensing device 48. The current sensing device 48 may include a differential amplifier circuit, which has, for example, an operational amplifier. In this case, the actual current value of the electric current, which flows in the resistor circuit 43, is sensed with the shunt resistor 47 and the current sensing device 48, and the microcomputer 41 executes the abnormality determination of the resistor circuit 43 based on the actual current value of the electric current.

Figure 9:
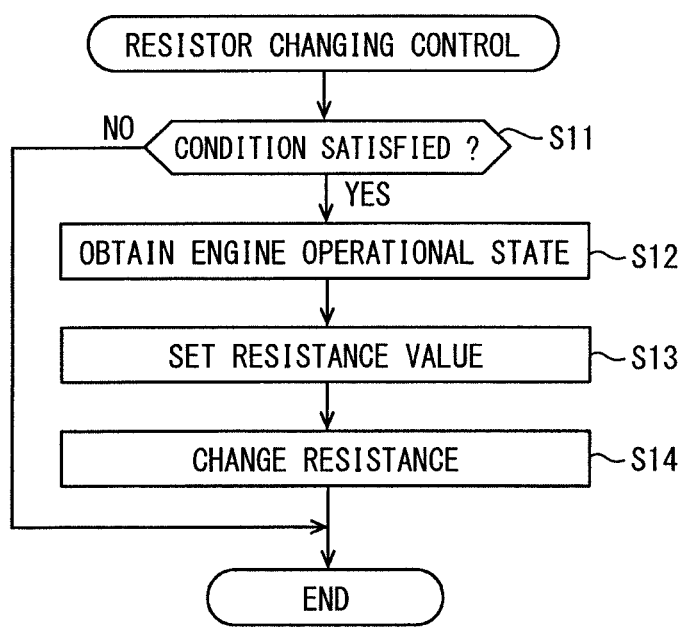
FIG. 9 is a flowchart showing a resistor changing control operation.

Next, a resistor changing control operation and an abnormality determination process, which are executed by the microcomputer 41, will be described with reference to flowcharts of FIGS. 9 and 11. FIG. 9 is the flowchart showing the resistor changing control operation. This process is repeated by the microcomputer 41 at predetermined time intervals.

In FIG. 9, at step S11, it is determined whether an execution condition for executing the resistor changing control operation is satisfied. For instance, the execution condition may include the followings: (I) the O₂ sensor 17 and the resistor circuit 43 are both normal; and (II) the sub-feedback control operation is currently executed. When the answer to the inquiry at step S11 is YES, the operation proceeds to step S12.

Figure 10:
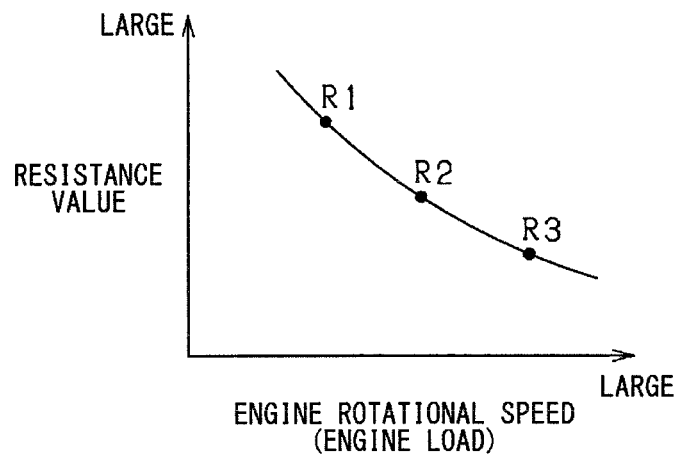
FIG. 10 is a diagram for setting a resistance value of a resistor circuit.

At step S12, the engine operational state, such as the engine rotational speed and/or the engine load (e.g., the amount of the intake air), is obtained. Thereafter, at next step S13, setting of the resistance value of the resistor circuit 43 is performed based on the engine operational state, which is obtained at step S12. At this time, the resistance value is set based on, for example, a relationship shown in FIG. 10. In FIG. 10, when the engine rotational speed or the engine load is increased, the resistance value to be set is reduced. In the case where the resistance values of the resistors 44a-44c are R1. R2 and R3, respectively, as shown in FIG. 8, for example, the resistance value R1 may be set in a low engine rotational speed range (a low engine load range), and the resistance valve R2 may be set in a middle engine rotational speed range (a middle engine load range). Furthermore, the resistance value R3 may be set in a high engine rotational speed range (a high engine load range).

Thereafter, at step S14, the on/off states of the switches 45a-45c are controlled to change the resistance value of the resistor circuit 43 based on the resistance value that is set at step S13. Upon execution of the changing of the resistance value of the resistor circuit 43, the current value of the electric current, which flows through the sensor element 31, is changed, and thereby the output characteristic of the $O_2$ sensor 17 is appropriately changed.

Figure 11:
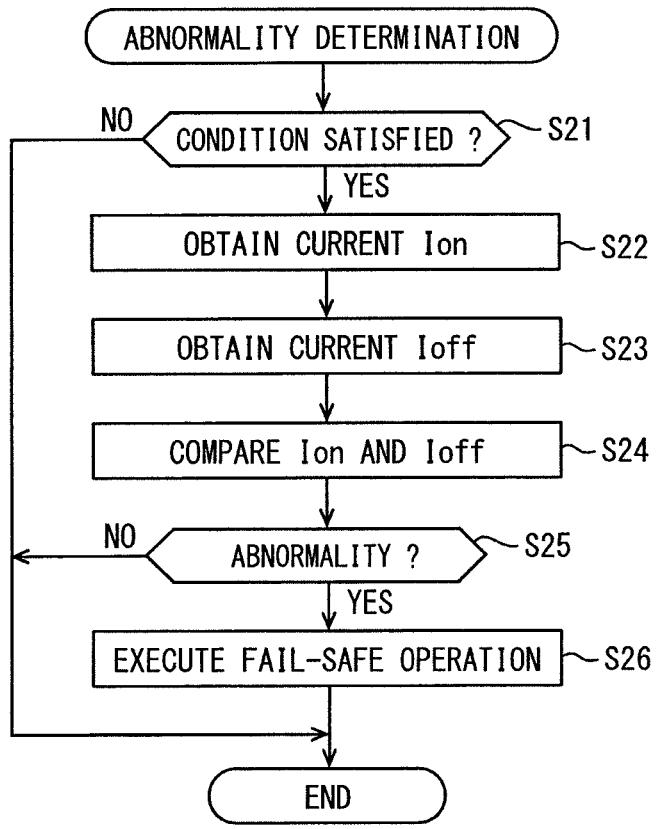
FIG. 11 is a flowchart showing an abnormality determination process for the resistor circuit.

FIG. 11 shows the flowchart indicating the abnormality determination process of the resistor circuit 43. This process is repeated at predetermined time intervals by the microcomputer 41.

In FIG. 11, at step S21, it is determined whether an execution condition for executing the abnormality determination process is satisfied. For example, this execution condition may include a condition of that the sensor element 31 is in the activated state, i.e., the temperature of the sensor element 31 is equal to or higher than the predetermined activation temperature. When the answer to the inquiry at step S21 is YES, the operation proceeds to step S22.

At step S22, an actual current value Ion of the electric current, which is sensed with the shunt resistor 47 and the current sensing device 48 in a state where only the corresponding one of the switches 45a-45c is turned on, is obtained. Thereafter, at next step S23, an actual current value Ioff of the electric current, which is sensed in a state where all of the switches 45a-45c are turned off, is obtained. Thereafter, at step S24, the actual current value Ion and the actual current value Ioff are compared with each other, and it is determined whether the abnormality of the resistor circuit 43 is present based on a difference between the actual current value Ion and the actual current value Ioff. Specifically, when the difference between the actual current value Ion and the actual current value Ioff is zero or is equal to or larger than a predetermined value (being excessively large), it is determined that the abnormality is present in the resistor circuit 43. Otherwise, it is determined that the resistor circuit 43 is normal (i.e., the abnormality is not present in the resistor circuit 43). At this time, in a case where each of the switches 45a-45c is not turned on/off in a normal manner, or abnormality, such as breaking or short-circuiting occurs in the corresponding electric path 60a-60c having the corresponding resistor 44a-44c, the difference between the actual current value Ion and the actual current value Ioff becomes zero or becomes equal to or larger than the predetermined value, so that it is determined that the abnormality is present in the resistor circuit 43.

The obtaining of the actual current value Ion of the electric current at step S22 may be preferably performed for each of the switches 45a-45c, and the abnormality determination at step S24 may be preferably executed for each of the switches 45a-45c.

Thereafter, at step S25. it is determined whether the result of the determination at step S24 indicates the presence of the abnormality. When the answer to the inquiry at step S25 is YES (i.e., the result of the determination at step S24 indicating the presence of the abnormality), the operation proceeds to step S26. At step S26, there is executed a fail-safe operation, such as stopping of the conduction of the electric current through the resistor circuit 43, stopping of the sub-feedback control operation of the air-to-fuel ratio, turning on of an abnormality warning lamp provided in, for example, an instrument panel, and/or storing of diagnosis data in a storage device (e.g., a memory).

The present embodiment discussed above provides the following advantages.

The sensor element 31 can be used as the battery by using the electromotive force of the sensor element 31. In view of this point, the electric current, which corresponds to the electromotive force of the sensor element 31, is conducted through the resistor circuit 43, which is provided in the electric path 70 (the electric paths 50a, 60) that connects between the atmosphere side electrode 34 and the ground at the time of generating the electromotive force in the sensor element 31. In this case, the electric current, which is similar to the above described electric current, flows between the two electrodes 33, 34 at the sensor element 31, and thereby the output characteristic of the $O_2$ sensor 17 is changed. In the above-described structure, the electric path 70 (the electric paths 50a, 60), which connects between the atmosphere side electrode 34 and the ground, and the resistor circuit 43, serve as the minimum required components for changing the output characteristic of the $O_2$ sensor 17. Thereby, while using the simple structure, the output characteristic of the $O_2$ sensor 17 can be changed in the appropriate desirable manner.

Through use of the resistor circuit 43, which is constructed in the above-described manner, the output characteristic of the $O_2$ sensor 17 can be adjusted to correspond with the air-to-fuel ratio at the point where the outflow of NOx begins at the first catalyst 15a. That is, in the case where NOx outflows from the first catalyst 15a, the $O_2$ sensor 17 can generate the corresponding electromotive force, which corresponds to the outflow of NOx from the first catalyst 15a. Therefore, the output characteristic of the $O_2$ sensor 17 can be appropriately changed, and thereby the NOx emissions can be limited.

The electric current I, which is conducted by the resistor 44 of the resistor circuit 43, shifts the equilibrium point of the gas reaction around the exhaust side electrode 33 of the $O_2$ sensor 17 to the NOx outflow point A2 (the second air-to-fuel ratio point) or the point adjacent to the NOx outflow point A2. Thereby, it is possible to implement the more appropriate structure for limiting the emissions of NOx through use of the output of the $O_2$ sensor 17.

Particularly, when the electric current I is supplied through the resistor 44 of the resistor circuit 43 in such a manner that the equilibrium point of the gas reaction around the exhaust side electrode 33 of the $O_2$ sensor 17 becomes slightly rich relative to the NOx outflow point A2 (the second air-to-fuel ratio point), the required robustness can be achieved to limit the NOx emissions.

The switch 45, which connects and disconnects between the atmosphere side electrode 34 and the resistor 44, is provided, and thereby it is possible to switch between the conducting state for conducting the electric current, which corresponds to the electromotive force, through the sensor element 31 and the non-conducting state for stopping the conduction of the electric current through the sensor element 31. In this way, the current value of the electric current, which is conducted through the sensor element 31, can be appropriately changed, and the abnormality determination can be appropriately achieved.

The on/off state of each switch 45a-45c is controlled based on the engine operational state to change the resistance value of the resistor circuit 43. In this way, even when the amount of the rich components in the exhaust gas is changed due to the change in the engine operational state, the output characteristic of the $O_2$ sensor 17 can be appropriately changed, and thereby the equilibrium point of the gas reaction around the exhaust side electrode 33 of the O₂ sensor 17 can be maintained at the desired point relative to the NOx outflow point A2.

The present disclosure is not necessarily limited to the above embodiment, and the above embodiment may be modified in various ways within the principle of the present disclosure. For example, the above embodiment may be modified as follows.

In the structure of FIG. 8, the resistor circuit 43 includes the three series circuits, and each of the series circuits includes the switch 45 (more specifically the switch 45a-45c) and the resistor 44 (more specifically the resistor 44a-44c), which are connected in series. However, the structure of the resistor circuit 43 is not necessarily limited to this and may be changed to any other suitable structure. For example, the switch 45 (more specifically the switch 45a-45c) may be eliminated to leave only the resistor 44 (more specifically the resistor 44a-44c) in one of the three series circuits. That is, as long as the switch 45 (more specifically the switch 45a-45c) is provided in at least one of the electric paths 60a-60c, it is possible to change the resistance value of the resistor circuit 43. Furthermore, the number of the series circuits, each of which includes the switch 45 (more specifically the switch 45a-45c) and the resistor 44 (more specifically the resistor 44a-44c), may be changed to one, two, four or more.

The structure, which changes the resistance value of the resistor(s) 44 (the current conducting resistor), may be constructed such that a plurality of resistors is connected in series in the electric path 70 that connects between the atmosphere side electrode 34 and the ground, and a switch is provided to each of the resistors in parallel with the resistor. Even in this structure, the resistance value of the resistor circuit 43 can be changed through opening/closing of each corresponding switch.

Figure 12:
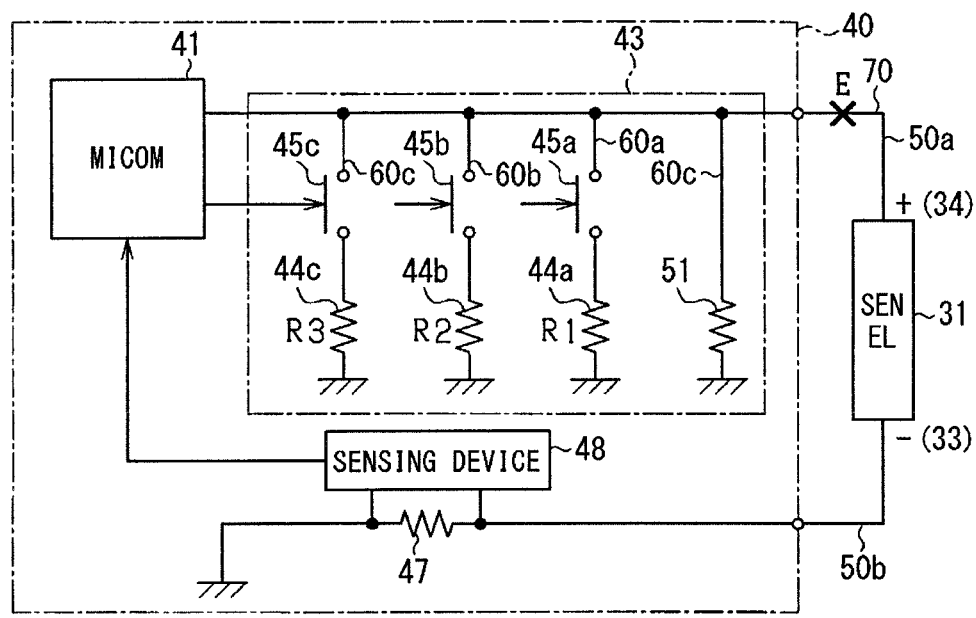
FIG. 12 is a diagram showing a structure of a sensor control arrangement in a modification of the embodiment.

The resistor circuit 43 may be constructed in a manner shown in FIG. 12, which indicates a modification of the above embodiment. In FIG. 12, a resistor (diagnosis resistor) 51 for sensing an abnormality is connected to the electric path 50a through an electric path 60c in parallel to the series circuits, each of which includes the switch 45 (more specifically the corresponding one of the switches 45a-45c) and the resistor 44 (more specifically the corresponding one of the resistors 44a-44c) connected in series. A resistance value of the diagnosis resistor 51 is, for example, 1 MΩ. In this structure, for instance, when breaking (cutting) of a conductive line occurs in a portion (see a point E of the electric path 50a in FIG. 12) of the electric circuit located between the sensor element 31 and the sensor control arrangement 40, the electromotive force input (A/D input) of the microcomputer 41 becomes a predetermined abnormal value (e.g., 0). Thereby, the abnormality, i.e., the breaking of the conductive line can be appropriately determined. At the time of determining the occurrence of the abnormality, i.e., the breaking of the conductive line, every switch 45 (more specifically every one of the switches 45a-45c) may be placed in the open state.

In the above embodiment, the O₂ sensor 17 is placed on the downstream side of the first catalyst 15a. Alternatively, the O₂ sensor 17 may be installed to an intermediate portion of the first catalyst 15a. In such a case, the O₂ sensor 17 may be installed to the substrate of the first catalyst 15a. In any of the above cases, it is only required that the O₂ sensor 17 is constructed to use the exhaust gas after the purification thereof at the first catalyst 15a as the sensing subject to sense the gas component(s).

Besides the O₂ sensor 17 having the above-described structure, the gas sensor may be a gas sensor that has a two-cell structure, which includes an electromotive force cell and a pump cell. In such a case, the output characteristic can be appropriately changed at the electromotive force cell of the two-cell type gas sensor.

What is claimed is:

1. A gas sensor control apparatus for a gas sensor, the gas sensor outputting an electromotive force signal corresponding to an air-to-fuel ratio of an exhaust gas of an internal combustion engine and including an electromotive force cell, which has a solid electrolyte body and a pair of electrodes, wherein the solid electrolyte body is held between the pair of electrodes that include a reference side electrode, which becomes a positive side at a time of outputting an electromotive force from the electromotive force cell, and an exhaust side electrode, which becomes a negative side at the time of outputting the electromotive force from the electromotive force cell, the gas sensor control apparatus comprising:

a resistor circuit that includes a resistor, wherein the resistor is installed in an electric path, the electric path connected to the electromotive force cell, wherein when the electromotive force cell generates the electromotive force, the resistor conducts an electric current to change an output characteristic of the gas sensor;

a control device programmed to control the resistor circuit, wherein:

the gas sensor control apparatus is applied to an exhaust gas purifying device of the internal combustion engine;

the exhaust gas purifying device is installed in an exhaust device of the internal combustion engine and includes a catalyst that purifies NOx, which is a lean component of the exhaust gas, and a rich component of the exhaust gas;

the gas sensor is installed in the exhaust device at a location, which is in an intermediate portion of the catalyst or on a downstroke side of the catalyst, to sense the air-to-fuel ratio of the exhaust gas after purification of the exhaust gas with the catalyst:

the catalyst has a conversion characteristic, which indicates a relationship between the air-to-fuel ratio and a catalyst conversion efficiency of the catalyst;

the conversion characteristic of the catalyst includes a second air-to-fuel ratio point, which is a point of starting an outflow of the NOx from the catalyst and is located on a rich side of a first air-to-fuel ratio that forms a equilibrium point for the rich component and oxygen; and the control device controls the resistor circuit such that the resistor circuit induces a flow of the electric current having a current value, which corresponds to a difference between (i) the first air-to-fuel ratio point and (ii) the second air-to-fuel ratio point of the catalyst, through the electromotive force cell in the electric path.

2. The gas sensor control apparatus according to claim 1, wherein the output characteristic of the gas sensor is changed through conduction of the electric current, which is in a range of 0.1 mA to 1.0 mA, through the electromotive force cell, and a resistance value of the resistor is in a range of 200Ω to 10 kΩ.

3. The gas sensor control apparatus according to claim 1, wherein the resistor induces the flow of the electric current having the current value, which is required to shift an equilibrium point of a gas reaction around the exhaust side electrode of the electromotive force cell to the second air-to-fuel ratio point or an adjacent point that is adjacent to the second air-to-fuel ratio point, in the electric path.

4. The gas sensor control apparatus according to claim 3, wherein the resistor induces the flow of the electric current having the current value, which is required to shift the equilibrium point of the gas reaction around the exhaust side electrode of the electromotive force cell to a rich side of the second air-to-fuel ratio point, in the electric path.

5. The gas sensor control apparatus according to claim 1, comprising a switching device, which enables connection and disconnection between the reference side electrode and the resistor.

6. The gas sensor control apparatus according to claim 1, wherein:
the electric path, which is connected to the electromotive force cell, includes a plurality of electric paths, which are arranged in parallel;
the resistor is one of a plurality of resistors, which are installed in the plurality of electric paths, respectively; and
at least one of the plurality of electric paths includes a switching device, which enables connection and disconnection between the reference side electrode and a corresponding one of the plurality of resistors.

7. The gas sensor control apparatus according to claim 6, wherein each of the plurality of resistors, which are provided in the plurality of electric paths, respectively, has a resistance value that is different from a resistance value of each of the rest of the plurality of resistors.

8. The gas sensor control apparatus according to claim 6, wherein the control device controls an opening and closing state of the switching device based on an operational state of the internal combustion engine.

* * * * *